United States Patent
Pichl et al.

(10) Patent No.: US 6,576,124 B2
(45) Date of Patent: Jun. 10, 2003

(54) CHROMATOGRAPHY DEVICE

(75) Inventors: Ulf Pichl, Länna (SE); John Davis, Örsundsbro (SE)

(73) Assignee: Amersham Biosciences AB (SE)

( * ) Notice: Subject to any disclaimer, the term of this patent is extended or adjusted under 35 U.S.C. 154(b) by 112 days.

(21) Appl. No.: 09/803,487

(22) Filed: Mar. 9, 2001

(65) Prior Publication Data

US 2002/0125181 A1 Sep. 12, 2002

(51) Int. Cl.[7] .............................................. B01D 15/08
(52) U.S. Cl. ..................... 210/198.2; 210/232; 210/456
(58) Field of Search ............................. 210/198.2, 450, 210/456, 232, 238, 282; 96/101, 105

(56) References Cited

U.S. PATENT DOCUMENTS

| | | | | |
|---|---|---|---|---|
| 4,414,172 A | * | 11/1983 | Leason | 264/255 |
| 5,089,125 A | * | 2/1992 | Hart | 210/198.2 |
| 5,137,628 A | * | 8/1992 | Hart | 210/198.2 |
| 5,167,810 A | * | 12/1992 | Vassarotti | 210/198.2 |
| 5,423,982 A | * | 6/1995 | Jung Bauer | 210/198.2 |
| 5,578,221 A | * | 11/1996 | Janik | 210/767 |
| 5,868,931 A | * | 2/1999 | Janik | 210/416.4 |
| 6,171,486 B1 | * | 1/2001 | Green | 210/198.2 |
| 6,224,760 B1 | * | 5/2001 | Davies | 210/198.2 |
| 6,440,301 B1 | * | 8/2002 | Dobos | 210/198.2 |
| 6,444,122 B1 | * | 9/2002 | Van Davelaar | 210/198.2 |

* cited by examiner

*Primary Examiner*—Ernest G. Therkorn
(74) *Attorney, Agent, or Firm*—Royal N. Ronning, Jr.; Stephen G. Ryan (57) ABSTRACT

The present invention relates to a chromatography column 1 in which the net 129 and/or bed support 131 is integrally joined to a net retaining means, preferably a sleeve 135 that protrudes through the column end plate 5, and/or to a net retaining circumferential ring. Different net retaining means are also presented.

10 Claims, 8 Drawing Sheets

CHROMATOGRAPHY DEVICE

FIELD OF THE INVENTION

The present invention relates to chromatography columns and nets for such columns, of the types mentioned in the preambles of the independent claims.

PRIOR ART

Chromatography columns often contain a net to prevent media from escaping from the end cells which are used for radially distributing the fluid flowing in from a central inlet at one end of the column and for radially collecting the fluid for subsequent outputting from a central outlet at the opposite end of the column. These nets extend across substantially the whole internal diameter of the column. In the prior art the nets have been made of polymer materials and have been attached (with a supporting backing plate if required) to the central inlet resp. central outlet by means of screws or bolts. The screws or bolts are mounted with their heads on the side of the net facing away from the inlet, resp. outlet, and they pass through suitably sized holes in the net and are screwed into suitably threaded axial holes in the wall of the central inlet resp. outlet.

Alternatively nets have been attached by being mounted on a central inlet or outlet tubular port provided with an internal thread and a stop flange positioned on the outside of the port at a distance from the end where the net is to be mounted which is less than the thickness of the net. The net is then positioned against the flange with the end of the port extending into a central opening in the net. The net is held in place by a threaded end piece which has a tubular portion provided with a thread adapted to mate with the thread on the inside of the port, and a flange at one end which pushes the net against the flange on the port when the end piece is screwed up into the port.

A problem with these mounting methods is that once the net is mounted in a chromatography column then access to the end piece or mounting bolts is limited. When it becomes necessary to detach the tubular port from the net, it is necessary to dismantle the column in order to be able to unscrew the end piece or mounting screws from inside the column. This has the disadvantages that it is time consuming and, for reasons of hygiene, it is undesirable to dismantle a column. Alternatively, it is possible necessary to provide a special tool which can be inserted through the tubular port from the end outside the chromatography column and then expanded laterally in order to grip the flange or in some other way become attached to the flange in order to permit the flange and end piece to be rotated. This has the disadvantage that it is difficult for an operator to see the tool when manoeuvring it into place and it is possible for him to inadvertently damage the end piece, net or port while trying to get the tool to grip the end piece.

A further problem is that the heads of the mounting screws, resp. the end pieces, project into the bed media and interfere with the packing of the bed media.

Additionally, in order to prevent unwanted leakage between the central port and the net, the join between the net and a central port is normally provided with sealing means such as O-rings or gaskets. Similarly, at the outer circumference of the net, in order to prevent leakage between the net and the wall of the column or distributor cell, sealing means such as O-rings or gaskets are provided between the net and wall and/or distributor cell. A problem with such an arrangement is that, if the net is made of woven stainless steel, or sintered metal, it is very difficult to obtain a good seal, as the net surface is uneven and the O-ring or gasket cannot deform sufficiently to fill all the irregularities in the surface of the net. This is particularly problematic if the bed particles used in the column are less than 30 micrometers in diameter or length as they are able to pass through gaps between the O-ring or gasket and the net. This leads to a loss of bed media through these gaps and a loss of column performance.

SUMMARY OF THE INVENTION

According to the present invention, at least some of the problems with the prior art are solved by means of a device having the features present in the characterising part of the independent claims. Further advantages are obtained by the features mentioned in the dependent claims. The present invention will be illustrated below by means of descriptions of non-limiting examples of embodiments and the following figures.

DETAILED DESCRIPTION OF EMBODIMENTS ILLUSTRATING THE INVENTION

Figure 1A:
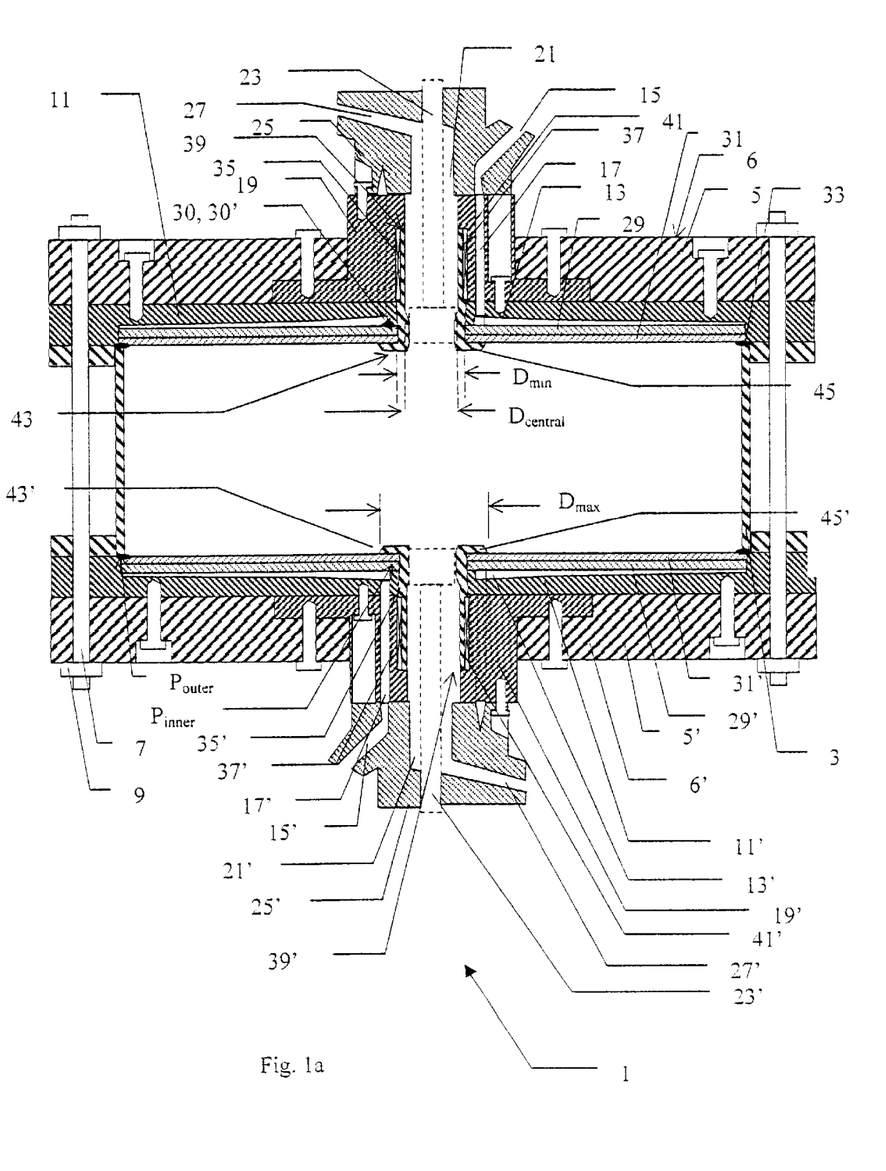
FIG. 1a) shows schematically a cross-section through a prior art chromatography column.

FIG. 1 shows schematically an embodiment of a prior art chromatography column 1. In this example the two ends of the column are substantially identical and either end can be used as the inlet end while the other end is used as the outlet end. For the sake of convenience and clarity of description, it will be assumed that the upper end of the column is the inlet end while the bottom end is the outlet end. Column 1 has a cylindrical wall 3 that has an end plate 5, 5' mounted on it at, respectively, the upper end 6 and the lower end 6' and these are held in place by external longitudinal threaded tie bars 7 with tensioning nuts 9. The space bounded by the wall 3 and end plates 5, 5' is intended to contain a bed medium (not shown). Each end plate 5, 5' supports a distributor cell 11, 11' on its side facing into the column 1. Each distributor cell 11, 11' has mobile phase distributing means, for example radially extending ribs 13, 13', for evenly distributing the mobile phase over the cross-section of the column 1 at the inlet end 6, and evenly collecting the mobile phase at the outlet end 6' from the cross-section of the column 1. The mobile phase is supplied to the column 1 via a mobile phase inlet 15 which is connected to longitudinal inlet bores 17 that open out onto the distributor cell 11.

Longitudinal bores 17 are formed in a valve block 19 mounted centrally on end plate 5. The mobile phase collected by the distributing means 13' is fed out of the column 1 via longitudinal outlet bores 17' that lead to a mobile phase outlet 15'. These longitudinal bores 17' are formed in a valve block 19' mounted centrally on end plate 5'.

Each valve block 19, 19' has a central through hole 21, 21' which accommodates a longitudinally movable hollow nozzle 23, 23' that can be used to inject slurry or cleaning fluid into the column. The though holes 21, 21' open out into the interior of the column. Nozzle 23 is supported in a coupling block 25 mounted on valve block 19, while nozzle 23' is similarly mounted in a coupling block 25' mounted on valve block 19'. Central through holes 21, 21' are each connected to a respective waste slurry outlet port 27, 27' in coupling blocks 25, resp. 25'.

Each end 6, 6' of the column is provided with a circular net 29, 29' that can be held against the respective distributor cell 11, 11' by a circular perforated bed support 31, 31'. Each net 29, 29' and bed support has a central hole 30, 30', 30'', 30''' with a diameter $D_{min}$ which is greater than the narrowest diameter $D_{central}$ of central through holes 21, 21'. The nets 29, 29' and bed supports 31, 31' are clamped around their outer circumferences Pouter between wall 3 and end plates 5, 5'. Sealing means such as O-rings 33 are provided to reduce leakage around the sides of the nets 29, 29' and bed supports 31, 31'. Nets 29, 29' and bed supports 31, 31 ' are each held against their respective distributor cell 11, 11' by their inner circumferences $P_{inner}$ by a means for retaining a net in the form of a central, flanged tubular sleeve 35, 35'. Each sleeve has an external thread 37, 37' on an outer end 39, 39' which co-operates with an internal thread 41, 41' in central through holes 21, 21'. The inner end 43, 43' of each sleeve 35, 35' has a flange 45, 45' which has an outside diameter $D_{max}$ that is greater than the diameter of the central holes 30–30''' in the nets 29, 29' and bed supports 31, 31 ' and it is these flanges 45, 45' that hold the nets 29, 29' against their respective distributor cells 11, 11'.

Figure 1B:
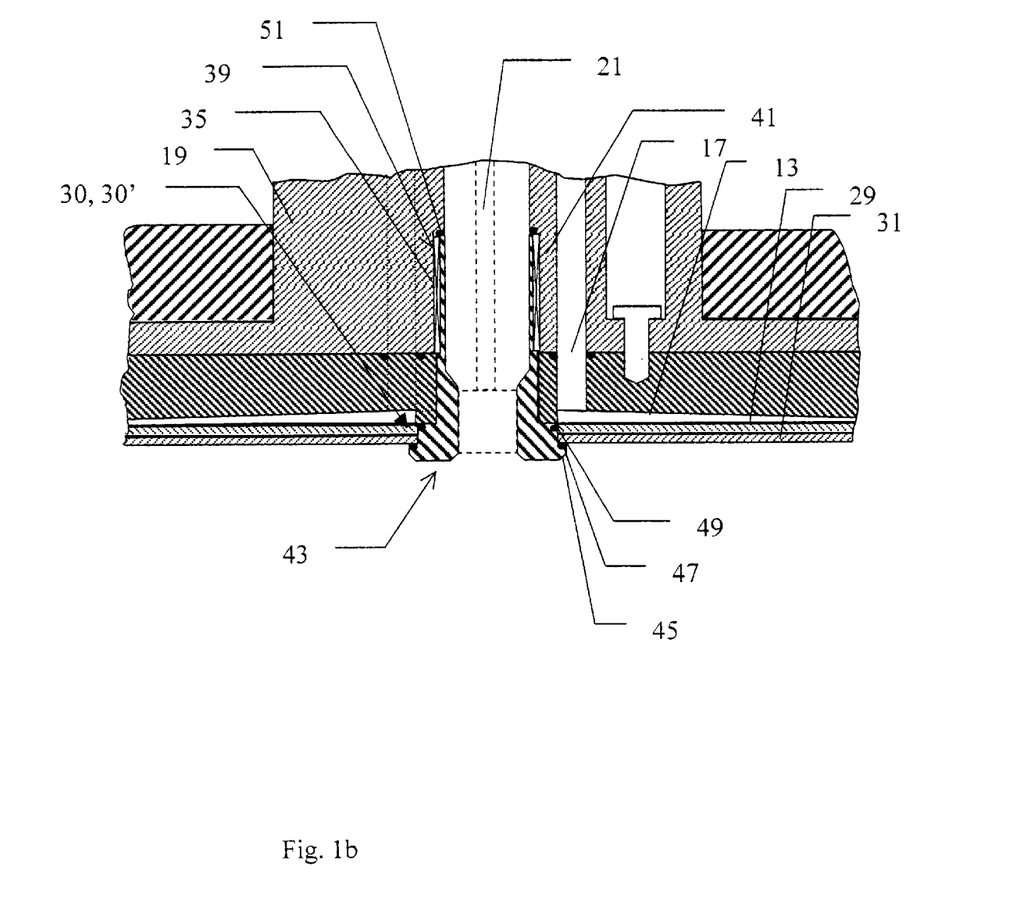
FIG. 1b) shows schematically an enlarged view of the central net mounting of the prior art column of FIG. 1a)

As can be seen in FIG. 1b), sealing means such as O-rings or gaskets 47, 49, 51 are provided to prevent leakage between the tubular sleeve 35 and the net 29, bed support 31 and valve block 19.

Figure 2A:
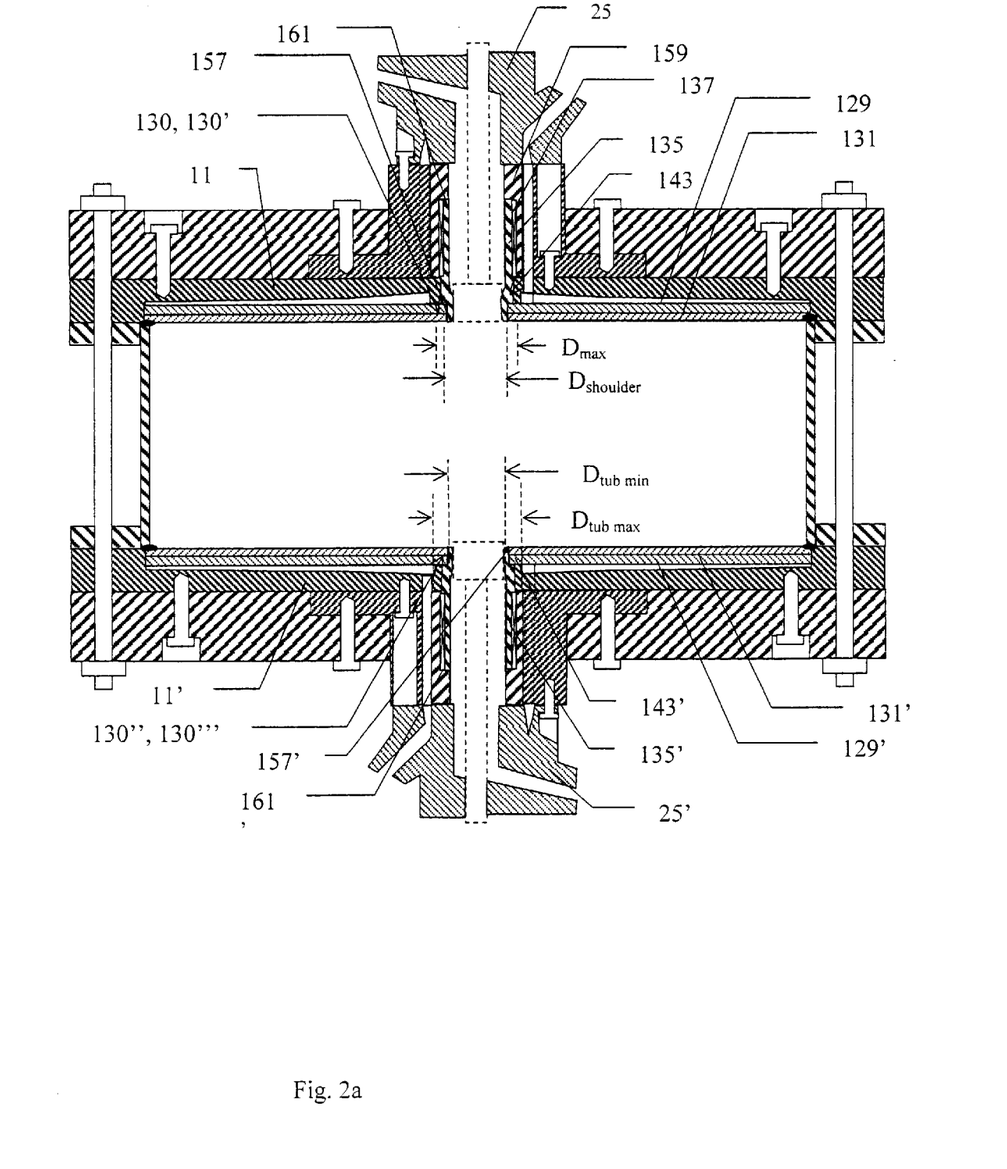
FIG. 2a) shows schematically a cross-section through an embodiment of a chromatography column in accordance with the present invention.
Figure 2B:
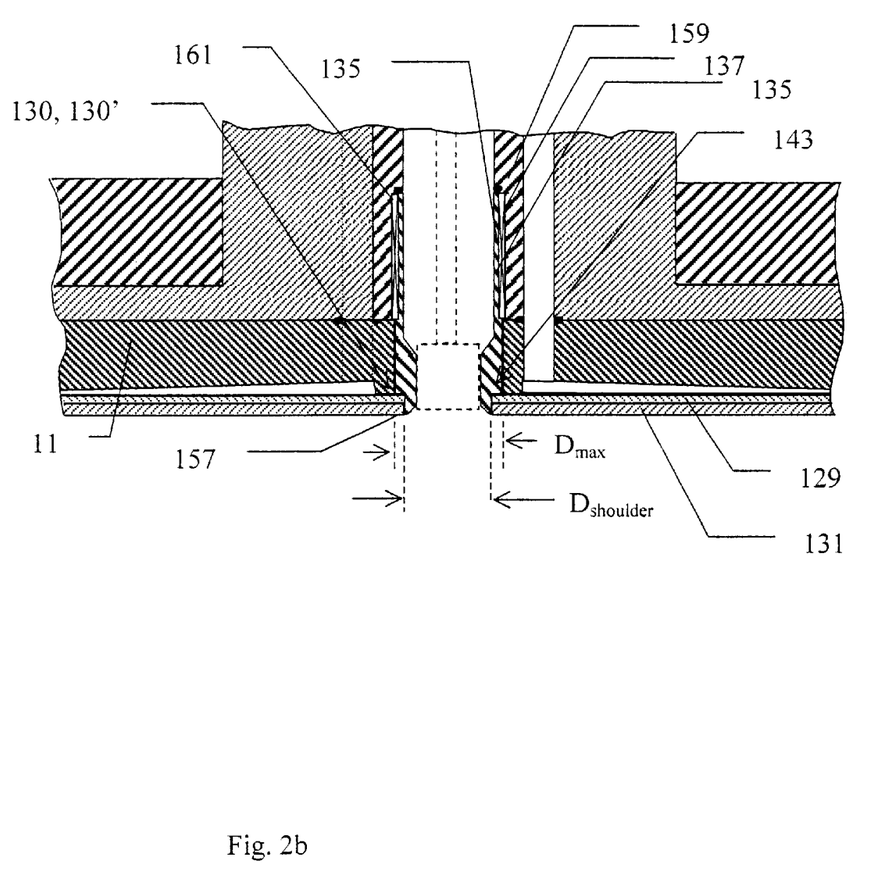
FIG. 2b) shows schematically an enlarged view of a first embodiment of the central net mounting of the column of FIG. 2a)

FIGS. 2a) and 2b) show an embodiment of a net mounting in accordance with the present invention, wherein the same reference numbers as used in respect to FIGS. 1a) and 1b) are used for corresponding components in FIGS. 2a) and 2b). In accordance with the present invention, instead of using a flanged tubular sleeve to hold the nets in place, a means for retaining a net by its inner circumference comprises a stepped sleeve 135, 135'. In a preferred embodiment of the invention the inner end 143, 143' of each sleeve is provided with a locating shoulder 157, 157' that has a diameter $D_{shoulder}$ that is less than the outer diameter $D_{max}$ of the rest of the sleeve 135, 135' and which is substantially the same as the diameter of the central holes 130–130''' in the nets 129, 129' and bed supports 131, 131'. The sleeves 135, 135' are made of a material which is compatible with the material of nets 129, 129' and bed support 131, 131' and they are joined together by welding. This has the advantage that the molten weld material flows into any gaps, such as pores in the nets 129, 129', between the sleeves 135, 135' and the nets 129, 129', and when it solidifies it seals these gaps, thereby preventing fluid or bed media from leaking past the sleeves 135, 135'. This avoids the use of O-rings or gaskets which leads to improved reliability and makes mounting the device easier. Thus the means for retaining the net also act as means for sealing the inner circumference of the net. In order to enable the valve block 119 to be easily removed it is preferable that the stepped sleeves 135, 135' are not screwed directly into the valve block 119, 119' but instead they are screwed into separate retaining means such as tubular sleeves 159, 159' which are held in place by the valve block but which are free to rotate with respect to the valve block. In this case the stepped sleeves 135, 135' can be provided with an external threaded portion 137, 137' which co-operates with an internal threaded portion 161, 161' in the tubular sleeve 159, 159', or vice versa. The tubular sleeves 159, 159' have an outside diameter $D_{tub\ max}$ which is greater than the diameter of the through holes 121, 121'extending through the end plates 11. The tubular sleeves 159, 159' have an inside diameter $D_{tub\ min}$ which is less than the diameter of the though holes 121, 121' extending through the end plates 11. The stepped sleeves 135, 135' have an outside diameter which is less than the diameter of the through holes 121, 121 extending through the end plates 5, 5', and which has a threaded portion which can co-operate with the threaded portion of the tubular sleeves 159, 159'. The stepped sleeves 135, 135' can project up outwards through the through holes 121, 121' in the end plates 5, 5' and have a tubular sleeve 159, 159' threaded onto them. Each tubular sleeve 159, 159' can then be rotated so that it travels along the thread on its respective stepped sleeve 135, 135 ' until the bottom edge of the tubular sleeve 159, 159' comes into contact with the end plate 5, 5'. The tubular sleeve 159, 159' can then be tightened against the end plate 5, 5' in order to pull the net 129, 129' against the distributor cell 11, 11' and end plate 5, 5' with the force necessary to ensure good operation of the column 1. The stepped sleeves 135, 135' can be prevented from rotating when the tubular sleeve 159, 159' is being tightened by the outer circumference $P_{outer}$ being clamped between wall 3 and end plates 5, 5'.

The tubular sleeve is preferably made from a material, or has threads made from a material, that can be threaded onto the stepped sleeve without galling and without the use of any lubricating substance in order to avoid introducing contaminants into the column. It may therefore be made of a polymer such as PEEK, Teflon® of the like.

These tubular sleeves 159, 159' are retained in central openings 121, 121' in the valve blocks 119, 119' and when the column is assembled they may clamped in the longitudinal direction between the end plates 11, 11' and the coupling blocks 25, 25' in order to prevent loosening during service.

It is of course possible to attach the stepped sleeves directly to the valve block, without the use of a tubular sleeve.

Figure 2C:
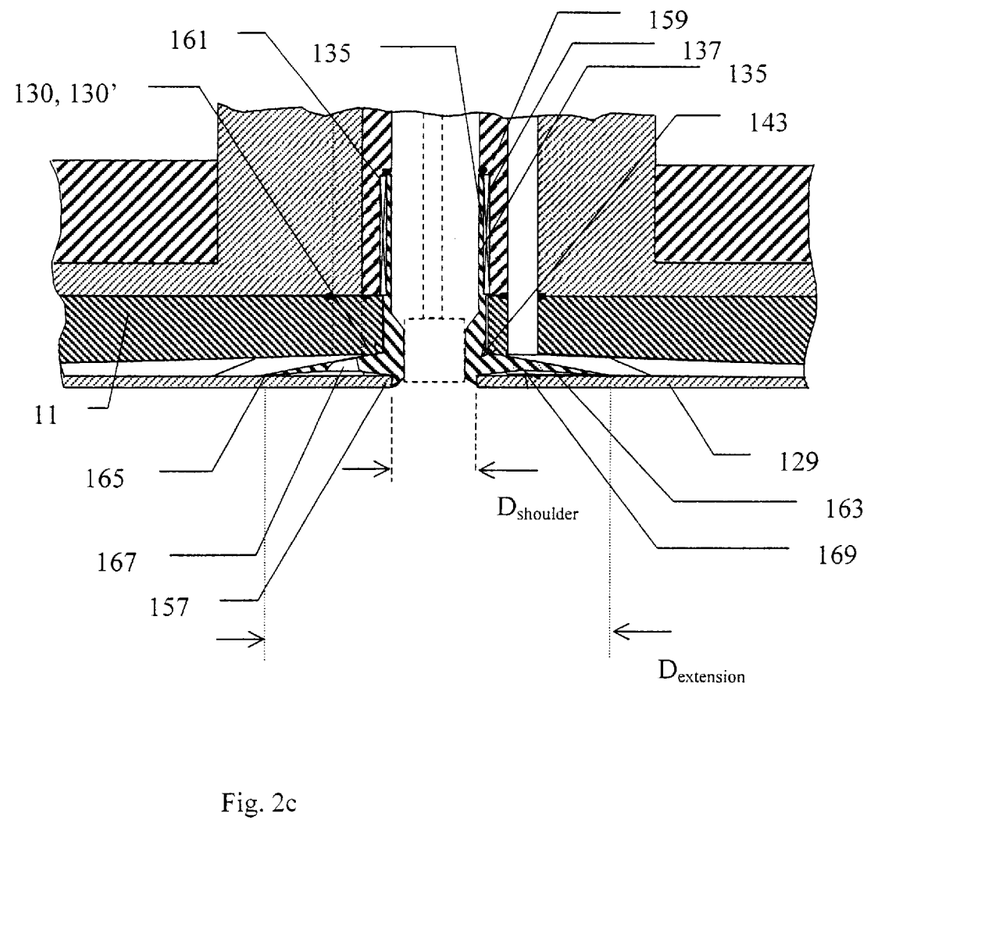
FIG. 2c) shows an enlarged view of a second embodiment of a central net mounting in accordance with the present invention.

FIG. 2c) shows a second embodiment of a means for retaining a net 135 which also has net supporting means 163 for supporting the net 129 at a distance intermediate its inner and outer circumferences. The net supporting means comprises a saucer shaped (or domed) flange 163 which extends a distance $D_{extension}$ from the center of the net 129 and which is welded, or by some other means, joined to the net around its circumference. As flange 163 is domed, it is substantially only in contact with the net at its circumference and a space 169 is left between the side of the flange 163 facing the net and the net 129. At least one through hole 167 is arranged in the flange 163 to allow fluid to pass though the net under the flange, thereby maximising the usable area of the net.

A comparison between FIGS. 1 and 2 shows that with the present invention the surface area of the column which is blocked by means for retaining a net is considerably smaller than that covered by the flange used in the prior art method.

This leads to better column performance. Additionally, there are no seals between the net and the net support in the present invention, as the joining of the net to the net support automatically seals this region and therefore the risk of leaks at this region is eliminated.

Figure 3A:
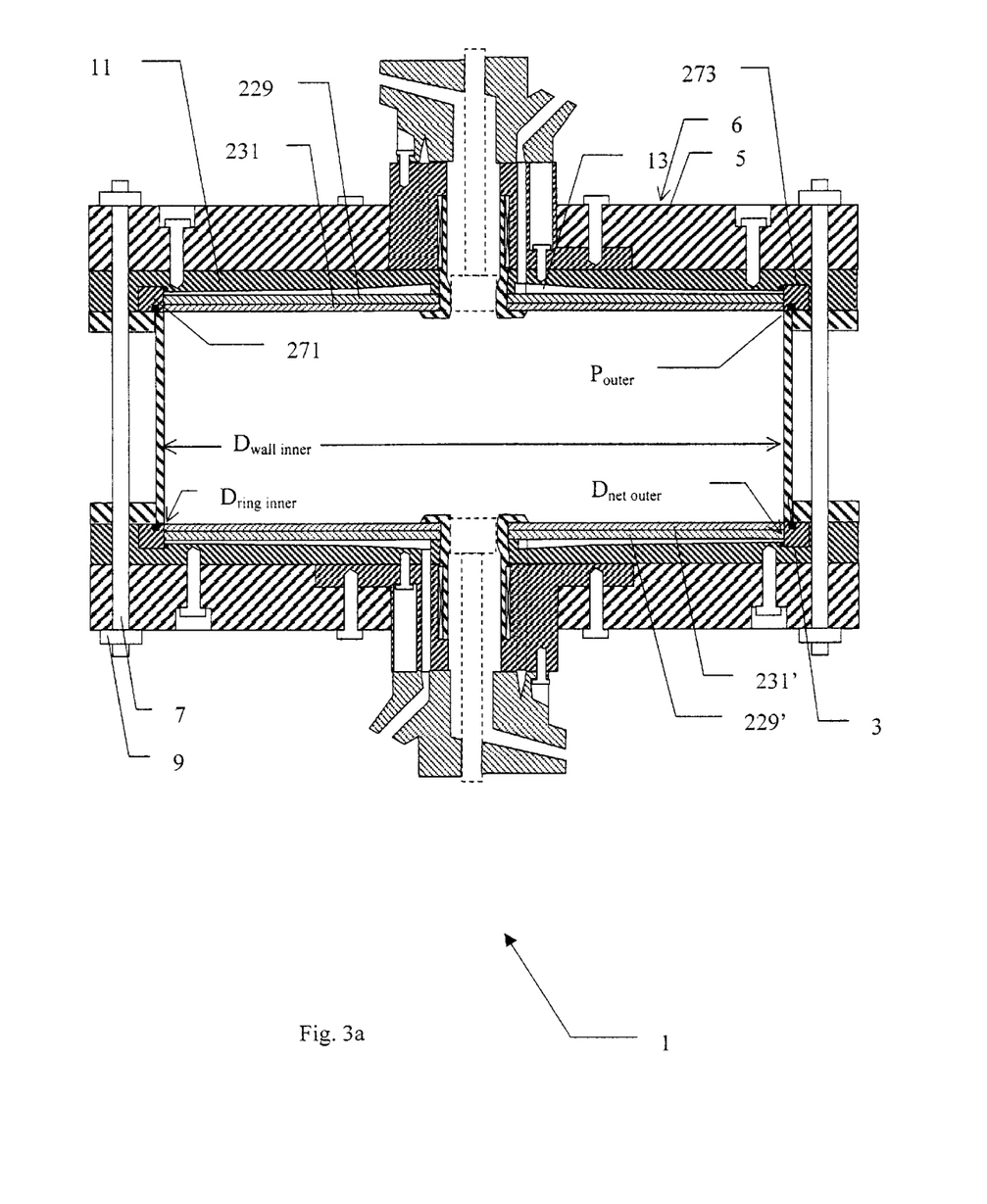
FIG. 3a) shows schematically a cross-section of a second embodiment of a chromatography column in accordance with the present invention.
Figure 3B:
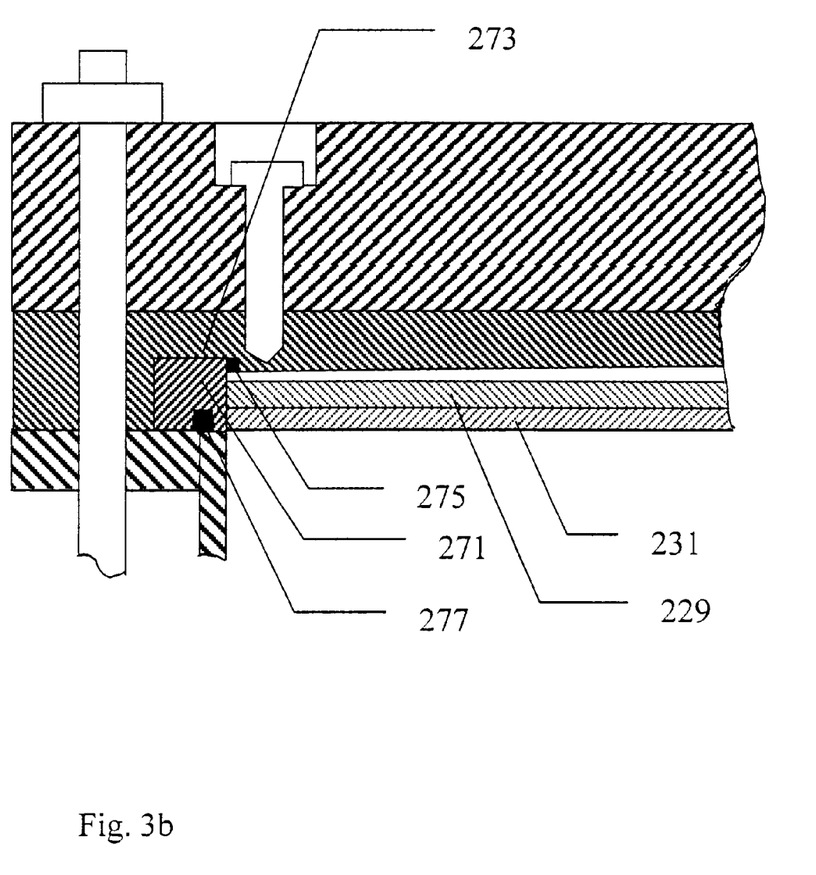
FIG. 3b) shows an enlarged view of the peripheral net mounting of the column of FIG. 3a); and, FIG. 4 shows a third embodiment of the present invention.

FIGS. 3a) and 3b) show an embodiment of the present invention in which the outer circumference $P_{outer}$ of each of the nets 229, 229' have means for retaining a net at its outer circumference 271, 271'. In this embodiment, the means for retaining the net 271, 271' comprises a ring 271, 271 ' of material integrally joined to the outer circumference $P_{outer}$ of the net. Preferably each ring is made of the same material as the net that it is joined to and the joining is performed by welding, or by the ring and net being formed in one piece, so that the risk of leakage between the net and ring is eliminated. Preferably the ring 271, 271 ' has an inner diameter $D_{ring\ inner}$ which is substantially the same as the outer diameter of the net $D_{net\ outer}$ and the inner diameter of the wall $D_{wall\ inner}$ so that the net extends across the whole internal diameter of the column, thereby maximising the area used for distributing or collecting fluid. The ring 271, 271' is clamped, or attached in any other suitable way, between the ends of the wall 3 and an appropriately sized and positioned annular groove 273, 273' formed in the distributor cell 211, 211'. Suitable sealing means such as O-rings or gaskets 275, 275', 277, 277' are provided between the contact surfaces of the ring 271, 271' and the distributor cell 211, 211 ' and the ring and the end of the wall 3. As these surfaces can easily be made substantially smooth, leakage at the outer circumference of the net can be easily avoided. It should be noted that the present invention is also applicable to columns with non-circular cross-sections, e.g. square or rectangle cross sections, and therefore the term "ring" is not intended to be limited to circular means for retaining a net but is also intended to include means for retaining a net having other shapes e.g. square, rectangular etc.

While in the preferred embodiment of the ring in accordance with the present invention the ring has an inner diameter which is substantially the same as the outer diameter of the net, it is conceivable that the ring has an inner diameter which is less than the outer diameter of the net and that the ring is attached to a top or bottom surface of the ring instead of being attached to the circular inner surface of the ring.

Figure 4:
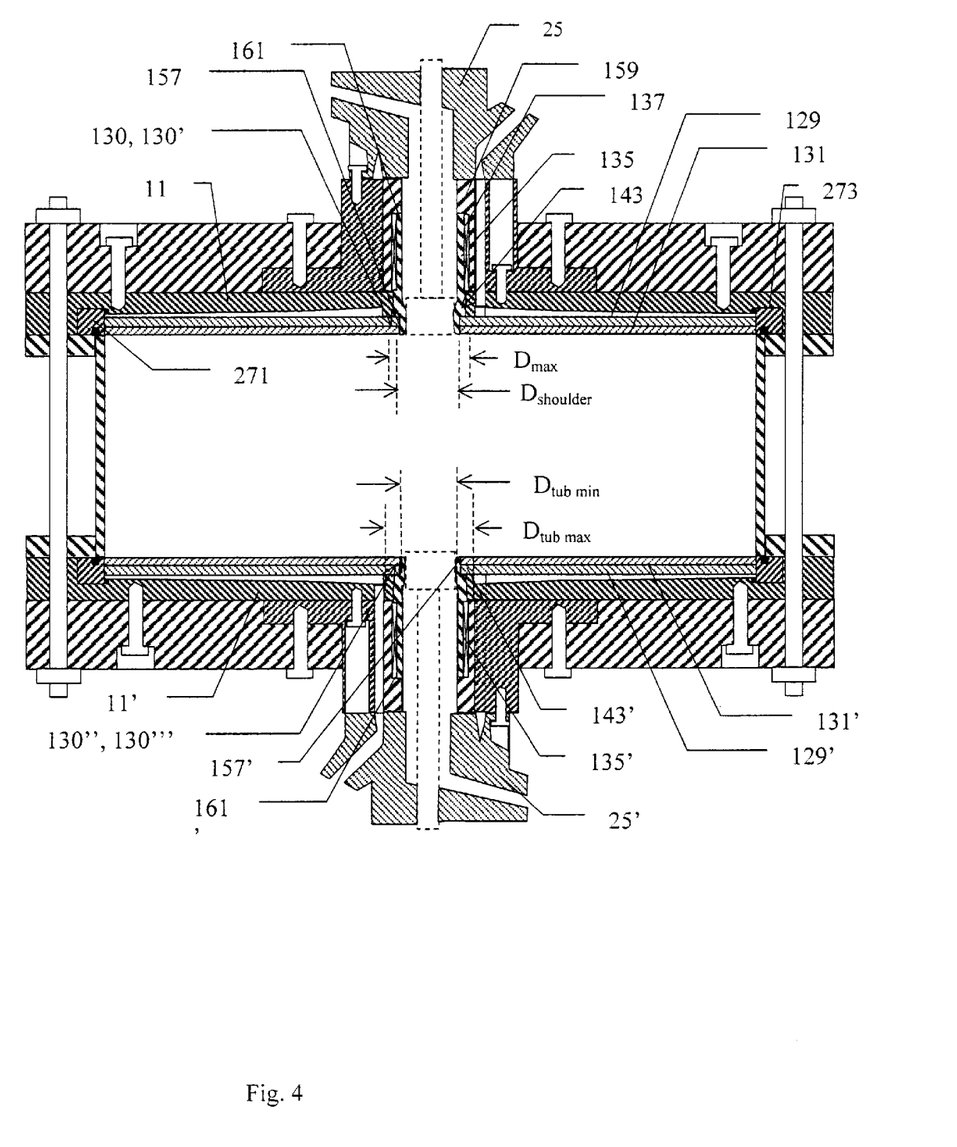

In a further embodiment of the present invention, shown in FIG. 4, a net is provided with a central means for retaining a net of the type described in connect with FIGS. 2a) and 2b) as well as a peripheral means for retaining a net of the type described in connection with FIGS. 3a) and 3b).

The present invention is not limited to use with metal nets and metal means for retaining a net welded together but is also applicable to plastic nets and plastic means for retaining a net that may also be welded together. While the invention has been illustrated by the use of welding to join the net and means for supporting the net together it is also conceivable to use any other inherently leak-proof means of joining the net and means for retaining a net such as soldering, brazing, gluing or the like, although welding is the preferred method as it does not introduce any impurities or unwanted substances into the column. It is also conceivable that the nets and means for retaining a net may be formed integrally, for example, by being cast, sintered or moulded in one piece.

Additionally, it is conceivable that the means for retaining a net is not integrally joined to the net but is instead integrally joined to a bed support that also supports a net. It is also conceivable that both the bed support and the net are integrally joined to the means for retaining a net.

It is apparent that many modifications and variations of the invention as hereinabove set forth may be made without departing from the spirit and scope thereof. The specific embodiments described are given by way of example only, and the invention is limited only by the terms of the appended claims.

What is claimed is:

1. A chromatography column comprising an end plate (5, 5') having two sides with a central through hole, said end plate being joined to a valve block (19, 19') with a central through hole (21, 21'); a net (129, 129', 229, 229') with a central hole (130–130''') with an inner circumference; and, a means for retaining a net (135, 135', 271, 271') characterised in that said means for retaining a net (135, 135') includes a sleeve having an inner end (143, 143') which is integrally joinable to said net at said inner circumference of said central hole (130–130'''), a tubular portion that is adapted to pass through said through hole in said end plate, and an outer end adapted to co-operate with a retaining means (159, 159') positioned on the side of the end plate opposite to the side facing the net wherein said retaining means (159, 159') is free to rotate with respect to said valve block.

2. The chromatography column of claim 1 wherein said net is welded to said means for retaining a net (135, 135', 271, 271').

3. The chromatography column of claim 1 wherein said means for retaining a net (271, 271') further comprises a ring (271, 271') attached to or near to the outer circumference of the net (229, 229').

4. The chromatography column of claim 1 wherein said retaining means includes a sleeve (159, 159') with an outer diameter greater than the diameter of said through hole in said end plate (5, 5').

5. The chromatography column of claim 4 wherein said sleeve (159, 159') is positioned inside said valve block.

6. A chromatography column comprising an end plate (5, 5') having two sides with a central hole, said end plate being joined to a valve block (19, 19') with a central through hole (21, 21'); a net (129, 129', 229, 229') with a central hole (130–130''') with an inner circumference; a bed support (131, 131', 231, 231') with a central hole; and, a means for retaining a net (135, 135', 271, 271'), characterised in that said means for retaining a net (135, 135') includes a sleeve having an inner end which is integrally joinable to said bed support (131, 131', 231, 231') at said inner circumference of said central hole, a tubular portion that is adapted to pass through said through hole in said end plate, and an outer end adapted to co-operate with a retaining means (159, 159') positioned on the side of the end plate opposite to the side facing the net wherein said retaining means (159, 159') is free to rotate with respect to said valve block.

7. The chromatography column of claim 6 wherein said bed support (131, 131', 231, 231') is welded to said means for retaining a net.

8. The chromatography column of claim 6 wherein said means for retaining a net further comprises a ring (271, 271') attached to or near to the outer circumference of the bed support (231, 231').

9. The chromatography column of claim 6 wherein said sleeve (159, 159') is positioned inside said valve block (19, 19').

10. The chromatography column of claim 9, wherein said means for retaining a net includes a sleeve with an outer diameter greater than the diameter of said through hole in said end plate.

* * * * *